United States Patent [19]

York

[11] Patent Number: 5,008,102

[45] Date of Patent: Apr. 16, 1991

[54] BIOCOMPATIBLE INTRAOCULAR LIGHT-SCREENING COMPOSITIONS AND METHODS OF INTRAOCULAR LIGHT SCREENING

[76] Inventor: Kenneth K. York, 2300 N. Edgemont, Los Angeles, Calif. 90027

[21] Appl. No.: 137,247

[22] Filed: Dec. 23, 1987

Related U.S. Application Data

[63] Continuation-in-part of Ser. No. 833,896, Feb. 26, 1986, abandoned.

[51] Int. Cl.$^5$ .................... A61K 7/40; A61K 7/42
[52] U.S. Cl. .................... 424/59; 351/161; 351/162; 351/163; 351/160 R; 351/160 H; 427/2; 514/912; 514/149; 623/6
[58] Field of Search .............. 514/912, 914; 351/160, 351/161, 162, 163; 623/6; 427/2, 59

[56] References Cited

U.S. PATENT DOCUMENTS

| | | | |
|---|---|---|---|
| 3,516,720 | 6/1970 | Mauer | 351/163 |
| 4,264,493 | 4/1981 | Battista | 351/161 |
| 4,328,803 | 5/1982 | Pape | 128/276 |
| 4,486,440 | 12/1984 | Emanuel et al. | 514/912 |
| 4,576,453 | 3/1986 | Borowsky | 351/162 |
| 4,636,212 | 1/1987 | Posin et al. | 351/162 |
| 4,657,363 | 4/1987 | Neefe | 351/162 |
| 4,669,834 | 6/1987 | Richter | 351/162 |
| 4,681,412 | 7/1987 | Lemelson | 351/162 |

FOREIGN PATENT DOCUMENTS

| | | | |
|---|---|---|---|
| 272524 | 7/1969 | Austria | 424/60 |
| 675784 | 12/1963 | Canada | 424/60 |
| 707525 | 4/1932 | France | 424/59 |
| 2073437 | 1/1971 | France | 514/912 |
| 2315949 | 1/1977 | France | 514/912 |
| 8602548 | 5/1986 | PCT Int'l Appl. | 514/912 |

OTHER PUBLICATIONS

Nuritdinor, Chem. Abs., 1981, vol. 94, p. 52832h.
Nutridinov (I), Chem. Abs., 1981, vol. 95, p. 49335p.
Emsley, The Optician, vol. 137, 6/1959, pp. 543-548.
"Antara" brochure, 1962, GAF Corp.,
"Polyacrylamide as a Basis for Medicinal Eye Films," by V. A. Nuritdinov, Chem. Abstracts, vol. 94, No. 8, 2/23/81, p. 364.
"Ultraviolet-Absorbing Chromophores...", by H. M. Clayman, Pharmaceuticals, vol. 105, Nov. 20, 11/17/87, p. 377.

Primary Examiner—Dale R. Ore

[57] ABSTRACT

Temporary, light-absorbing, ocularly biocompatible compositions include at least one biocompatible, light-absorbing substance in an amount sufficient to block substantially all light of desired wavelengths and protect susceptible ocular tissues from light induced damage, where the composition is placed introcularly between the light source and ocular tissues susceptible to damage from such light. These compositions can be used to coat or to impregnate intraocular lenses, either before or after insertion of the lenses into the eye, or can be placed intraocularly, in the anterior chamber, over the pupil, in the posterior chamber or in the capsular bag of an eye, as during an ophthalmic procedure. Where the composition includes a viscous, biocompatible, space-maintaining substance such as sodium hyaluronate, chondroitin sulfate, methylcellulose or polyacrylamide, the composition also protects the endothelium, maintains space within the eye, moves tissues, allows focal application of the light-absorbing substance, and permits rapid reversal or pupillary occlusion.

10 Claims, No Drawings

BIOCOMPATIBLE INTRAOCULAR LIGHT-SCREENING COMPOSITIONS AND METHODS OF INTRAOCULAR LIGHT SCREENING

This application is a continuation in part of U.S. patent application serial number 833,896, filed Feb. 26, 1986 in the U.S. Patent and Trademark Office, and entitled Biocompatible, Intraocular Light-Screening Substances, now abandoned.

This invention relates to temporary biocompatible, light-absorbing compositions used intraocularly to protect light-sensitive ocular tissues from photic damage during therapeutic and diagnostic ophthalmic procedures. These compositions absorb or block substantially all light of desired wavelengths which can include ultraviolet (UV), visible and/or infrared radiation, when placed intraocularly between the source of the potentially damaging light and ocular tissues susceptible to damage from such light. A preferred embodiment would absorb predominantly damaging short wavelength visible light (i.e. light having wavelengths in the range of about 400 to about 500 nm, i.e., blue). For example, these compositions can be placed in the anterior chamber of an eye over the pupil, on an intraocular lens (IOL), in the posterior chamber or in the capsular bag. These compositions are temporary and are eliminated from the eye over a relatively short period of time after application, varying from minutes to days, without substantial damage to such tissue.

The biocompatible, light-screening compositions include at least one chromophore, chromogen, or dye (such as Fluorescein Sodium (Spiro [isobenzofuran-1(3H), 9'-(9H]xanthene]-3-one, 3'6'-dihydroxy, disodium salt) and/or beta carotene, which absorb strongly in the blue portion of the spectrum) or fine biodegradable pigment particles, or liposomes containing a light-screening substance which will form a suspension. These light absorbing substances can be mixed, or, where practicable, bonded chemically to a carrier substance, to facilitate application. These biocompatible compositions, in sufficient concentration, absorb substantially all light of desired wavelengths directed at them, and can be injected into the anterior chamber, posterior chamber or capsular bag of an eye or can be placed on an IOL to protect the lens, retina or other light sensitive ocular structures.

In preferred embodiments, this invention relates to a composition including at least one biocompatible, light-screening substance, such as Fluorescein Sodium, or beta carotene, or both, mixed or chemically bonded to a carrier substance, preferably a viscous, biocompatible, space-maintaining gel such as chondroitin sulfate, sodium hyaluronate, methylcellulose, hyaluronic acid or polyacrylamide. This preferred embodiment concentrates the light-screening substance, delays its dispersion, permits focal application, serves as a space maintaining viscoelastic agent and permits IOL coating or impregnation.

Contact with the corneal endothelium may be avoided, thus minimizing the risk of thermal and photosensitization damage to these critical cells. Suitable biocompatible, viscous, space-maintaining gels and other substances include, but are not limited to, solutions of chondroitin sulfate, sodium hyaluronate, methyl cellulose, hyaluronic acid, and polyacrylamide.

These compositions can be applied intraocularly over the miotic pupil of a supine patient to block light during an ophthalmic procedure. After the procedure, such as a laser procedure on the cornea, when the patient assumes an erect position, the composition, being denser than water, will fall into the inferior angle of the eye, clearing the visual axis, and allowing the patient to see. The temporary composition will be eliminated from the inferior angle of the eye without any deleterious effects through natural filtration means.

In preferred embodiments comprising at least one biocompatible light-absorbing substance and at least one carrier gel, the composition can vary, depending upon the nature of the light-absorbing substance and of the gel. For Fluorescein Sodium, a satisfactory mixture is one part 10% Fluorescein Sodium and 99 parts 1% sodium hyaluronate, but a wide range of concentrations is feasible. The light-absorbing substances and the carriers for these substances are, in preferred embodiments, mixed with one another under sterile conditions in the desired ratios and for a time sufficient to disperse the light-absorbing substances uniformly in the carriers. These substances may be combined as mixtures, or may be chemically bound.

Fluorescein Sodium is a particularly desirable light-absorbing substance because of its ocular biocompatibility, its long history of safe use in retinal angiography, and its capacity to strongly absorb light with wavelengths in the range of about 400 to about 500 nm. Moreover, Fluorescein Sodium is not a strong photosensitizer. Fluorescein Sodium does not absorb strongly in the red portion of the spectrum, and would permit viewing of a red laser or light for fixation.

The methods of this invention comprise forming an opening in the cornea or limbus of an eye of sufficient size to permit an ophthalmic cannula to pass through the opening, and then injecting the light-absorbing composition over the pupil of an eye before exposing the lens or retina of the eye to therapeutic or diagnostic ultraviolet light, visible light or infrared radiation. Alternatively, the capsular bag or posterior chamber may be filled with an intraocular light-absorbing composition to facilitate intraocular lens implantation and provide protection from light-induced retinal damage during surgery. The quantity of the light-absorbing composition placed over the lens can vary, but, in practice, need not exceed the amount necessary to occlude the pupil. Alternatively the IOL may be coated or impregnated with a temporary light absorbing composition to provide protection from light induced ocular damage without permanently altering the transmission characteristics of the IOL. The quantity of the composition and the concentration of the light-absorbing substance should be sufficient to prevent light induced ocular damage during a therapeutic or diagnostic ophthalmic procedure utilizing such light. Even intraocular lenses containing UV-absorbing compounds still transmit blue light, which has been shown to cause retinal damage.

The light-screening composition can also be applied to intraocular lenses in the form of one or more films on the lens surface, by impregnation into the lens, or both. Such incorporation and application can be done during manufacture of the lenses, after manufacture but before insertion into the eye, or after insertion into the eye. These films or coatings can be wet or dry. For example, a biocompatible light screening composition consisting of a carrier such as polyacrylamide and a biocompatible intraocular light-absorbing substance such as beta carotene and/or Fluorescein Sodium can be applied to an intraocular lens, and then dried to form a film on the IOL, producing an improved and convenient IOL product ready for insertion into a human eye. In a preferred embodiment, 99 parts of 4-5% polyacrylamide in a balanced salt solution is mixed with one part of 10% fluorescein sodium. This composition can be dried onto IOL's to form a coating. The polyacrylamide and Fluorescein Sodium can also be chemically bonded to delay dispersion.

The light-absorbing compositions in this invention are of particular importance in preventing or at least minimizing retinal damage in the form of cystoid macular edema (CME) and blue light photoretinitis (photochemical damage). CME and blue light photoretinitis are significant causes of permanent visual loss after cataract surgery. The intense light from coaxial illumination systems on operating microscopes during cataract surgery can cause retinal damage. Intraocular lenses that are implanted during most cataract operations exacerbate the problem by focusing and concentrating light on the macula, the most sensitive and visually important part of the retina. Wavelengths from about 290 nm to about 1,400 nm are transmitted through the cornea of the mammalian eye to the lens and retina. Ultraviolet light has more energy and causes more damage than the longer visible wavelengths. Similarly, the retina is much more susceptible to damage from blue light than infrared light. Three orders of magnitude more power is required to produce a minimal retinal lesion at 1,064 nm (infrared light) than at 441 nm (blue light).

Recognizing the hazard of short wavelength light, efforts to prevent photic damage have included the use of UV-absorbing and IR-absorbing microscope filters, eclipse microscopic filters, permanent UV-absorbing intraocular lenses, occluders placed on the cornea, and anti-inflammatory drugs. None of these methods has been entirely successful. By contrast, the temporary light-screening compositions of this invention can be placed over the pupil of an eye prior to certain anterior segment laser procedures such as photokeratomileusis, or in the capsular bag or posterior chamber prior to intraocular lens implantation, or over the intraocular lens before or after implantation. These light-screening substances will protect the crystalline lens, vitreous and/or retina from unintentional photic damage.

Many ophthalmic surgeons today use a viscoelastic preparation in every cataract extraction/lens implant that they perform to protect the corneal endothelium, maintain space and move tissue. The mucopolysaccharides, sodium hyaluronate and chondroitin sulfate absorb in the infrared spectrum, but not sufficiently in the particularly damaging long UV and short visible light spectra. The preferred embodiment of this invention can perform all the functions of conventional viscoelastic preparations and can conveniently be used as a IOL coating while protecting light sensitive ocular structures from photic damage.

What is claimed is:

1. A method of protecting ocular tissues such as, but not limited to, the lens, vitreous and retina of an eye from damage caused by light selected from the group consisting of ultraviolet light, short wavelength visible light, visible light, and infrared light, comprising placing intraocularly between the source of the light and said ocular tissues, in an amount sufficient to prevent a substantial amount of said light from reaching said tissues, a temporary light-absorbing or screening substance or composition substantially undamaging to intraocular eye tissues in an amount sufficient to absorb or screen said light, said substance or composition being adapted for elimination from intraocular eye tissues over a relatively short period of time after said placement.

2. The method of claim 1 wherein said composition comprises at least one carrier and at least one biocompatible, light-absorbing or screening substance.

3. The method of claim 1 wherein said carrier comprises at least one viscous, space-maintaining, biocompatible substance.

4. The method of claim 1 wherein said carrier comprises at least one viscous, space-maintaining, biocompatible substance and wherein the biocompatible, light-absorbing substance is a chromophore, a chromogen, a dye or a suspension of light screening particles.

5. The method of claim 1 wherein said viscous, space-maintaining, biocompatible carrier is a polyacrylamide, and wherein the biocompatible, light-absorbing substance is Fluorescein Sodium, such that the eye is protected from hazardous blue light.

6. The method of claim 1 further comprising placing said composition onto the surface of an intraocular lens in a hydrated or dehydrated state.

7. The method of claim 1 further comprising impregnating said composition into an intraocular lens.

8. An intraocular lens including a temporary light-absorbing, biocompatible composition, substantially undamaging to eye tissues, comprises at least one carrier and at least one light-absorbing substance in amounts sufficient to absorb or screen a substantial amount of light impinging on said lens, said light being selected from the group consisting of ultraviolet light, short wavelength visible light, visible light and infrared light, said composition being adapted for elimination from said lens and from intraocular eye tissues that receive said lens over a relatively short period of time after placement of said lens in said eye tissue.

9. The lens of claim 8 wherein said composition forms a coating on the surface of said lens.

10. The lens of claim 9 or claim 8 wherein said composition includes Fluorescein or beta carotene.

* * * * *